(12) United States Patent
Morken

(10) Patent No.: US 6,496,559 B1
(45) Date of Patent: Dec. 17, 2002

(54) SAMPLE PREPARATION FOR INSPECTION OF BALL CONTACTS AND INTERNAL VIAS

(75) Inventor: David Bruce Morken, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/661,038

(22) Filed: Sep. 13, 2000

Related U.S. Application Data

(60) Provisional application No. 60/214,430, filed on Jun. 28, 2000.

(51) Int. Cl.$^7$ ............................................. G01N 23/02
(52) U.S. Cl. ..................... 378/58; 356/237.4; 356/137.5
(58) Field of Search ................... 378/58; 356/237.4, 356/237.5; 382/149, 150; 348/126; 250/559.34

(56) References Cited

U.S. PATENT DOCUMENTS

| | | | |
|---|---|---|---|
| 5,015,097 A | 5/1991 | Nomoto et al. | 356/314 |
| 5,122,737 A | 6/1992 | Clauberg | 324/767 |
| 5,216,485 A | 6/1993 | Bird et al. | 356/394 |
| 5,288,991 A | 2/1994 | King et al. | 250/216 |
| 5,301,012 A | 4/1994 | King et al. | 356/398 |
| RE35,423 E * | 1/1997 | Adams et al. | 378/58 |
| 5,852,870 A * | 12/1998 | Freyman et al. | 29/841 |
| 5,900,645 A * | 5/1999 | Yamada | 247/48 |
| 5,977,641 A * | 11/1999 | Takahashi et al. | 257/778 |
| 6,151,380 A * | 11/2000 | Zweig et al. | 378/58 |
| 6,272,204 B1 * | 8/2001 | Amtower et al. | 378/63 |

OTHER PUBLICATIONS

Serway, Physics for Scientists & Engineers with Modern Physics, 1992, Saunders College Publishing, 3rd Ed., p. 975.*

* cited by examiner

*Primary Examiner*—Robert H. Kim
*Assistant Examiner*—Chih-Cheng Glen Kao
(74) *Attorney, Agent, or Firm*—McDermott, Will & Emery

(57) ABSTRACT

A method for performing inspection of raised electrical contacts, such as ball grid array (BGA) and "flip-chip" type contacts, and associated underlying vias, comprises steps of: providing an electrical or electronic device or component having a major surface including an array of closely spaced apart BGA or flip-chip type raised contacts with respective underlying vias; selecting an area-of-interest (AOI) including at least one BGA or flip-chip type contact/via structure; cutting through the device or component along parallel lines to form a narrow, elongated strip including the AOI; mounting the elongated strip on a transparent substrate; and performing X-ray radiographic analysis of the elongated strip to inspect the at least one BGA or flip-chip type contact/via structure for the presence of misalignments, voids, and delaminations.

18 Claims, 1 Drawing Sheet

SAMPLE PREPARATION FOR INSPECTION OF BALL CONTACTS AND INTERNAL VIAS

CROSS-REFERENCE TO PROVISIONAL APPLICATION

This application claims priority from U.S. provisional patent application Serial No. 60/214,430, filed on Jun. 28, 2000, the entire disclosure of which is incorporated herein by reference.

RELATED APPLICATION

This application contains subject matter similar to that disclosed in U.S. patent application Ser. No. 09/677,845, filed on Oct. 3, 2000.

1. Field of the Invention

The present invention relates to a method for performing inspection and analysis of electrical contacts and associated vias of electrical and electronic devices. More particularly, the present invention pertains to an improved method of sample preparation for performing X-ray analysis and inspection of "flip-chip" and/or ball grid contact arrays ("BGA") and their associated internal vias, such as are utilized in semiconductor integrated circuit ("IC") devices and circuit boards therefor, for determination of offset or misalignment, voids, and layer separation (i.e., delamination).

2. Background of the Invention

An increasingly important aspect of semiconductor IC manufacturing technology is mounting of the semiconductor IC chip or die to an appropriate substrate. Frequently, this requires providing the chip or die with as many input/output ("I/O") terminals as is possible. As a consequence of the requirement for a large number of terminals to be formed on a limited amount of chip or die surface, so called "flip-chip" structures and bonding techniques have been developed in order to provide high areal density interconnections between the IC chip or die and the substrate.

According to flip-chip methodology, the IC chip or die is mounted via direct bonding to a package substrate, e.g., an organic polymer-based or ceramic package substrate. Generally, the flip-chip process entails disposing a plurality of raised contacts, e.g., in the form of solder balls or bumps, on the upper major surface of the chip or die (termed a ball grid array, "BGA"), wherein the solder balls or bumps may overlie and connect with internal vias of the IC device. The IC chip or die is then "flipped" over so that the solder balls or bumps face and are mated with a corresponding ball grid array (BGA) or bonding pads on the substrate surface, which BGA or bonding pads may also overlie and electrically contact internal vias of the substrate for electrically connecting underlying metallization levels, patterns, etc. Once mated, the solder bumps or balls of the IC die or chip and the corresponding solder bumps or balls or bonding pads of the substrate are heated to effect reflow and mutual bonding, whereby each solder ball or bump forms a bond between the chip or die and the substrate. As a consequence, each bonded combination functions as both an electrical and physical contact.

According to flip-chip methodology, electrically conductive balls or bumps comprising a solder material are formed on the IC chip or die, as well as on the mating surface of the substrate. Bonding between the two sets of solder balls or bumps is effected by application of heat to the chip or die and the substrate. The application of heat causes both sets of solder-based balls or bumps to reflow, thereby providing physical and ohmic connection therebetween.

Flip-chip contact arrangements, such as described above, are susceptible to exhibiting poor ohmic contact performance and/or poor physical bonding, in extreme instances leading to device failure. Poor ohmic resistance and/or poor physical bonding may result from a number of factors, including, inter alia, offset or misalignment of the solder ball or bump forming the external, raised contact, and the underlying internal via structure; presence of voids in the ball/via structure, whether arising during manufacture or subsequent thereto as a result of, e.g., electromigration of one or more metallic elements or components thereof; and layer separation, i.e., delamination, oxidation and/or disbonding of e.g., the solder ball or bump and the underlying via due to compositional differences which result in poor mutual adhesion.

As a consequence of the above-described several possible, but distinct, scenarios or mechanisms leading to poor performance of BGA and flip-chip contact/via structures, inspection and/or failure analysis is generally necessary for determining the particular mechanism responsible for poor performance or failure of a particular device or component. However, methodology for performing simple, reliable, and rapid sample reparation for visual or X-ray radiographic failure analysis and/or inspection of a particular area-of-interest (AOI) of a BGA or flip-chip array with associated underlying vias is presently unavailable. Moreover, a convenient method for performing high magnification, visual and/or X-ray inspection and/or analysis of an AOI of a BGA or flip-chip array of either or both of a semiconductor IC chip or die and circuit board therefor, is similarly presently unavailable.

Accordingly, there exists a need for improved methodology for simple, reliable, and rapid sample preparation for facilitating performing high magnification level, visual and/or X-ray radiographic inspection and/or analysis of solder ball/underlying via structures of a particular AOI of a semiconductor IC chip or die or circuit board therefor, which methodology is capable of revealing all pertinent internal structural features of e.g., flip-chip devices and contacts, and does not require costly, specialized, or customized equipment or apparatus.

The present invention, wherein a particular AOI of a BGA or flip-chip array of solder ball contacts/underlying vias of an IC die or chip or circuit board therefor is isolated and removed therefrom in elongated, narrow strip form and mounted on a transparent substrate, which in turn is held by a rotatable/tiltable gripping means, e.g., a rotatable/tiltable chuck, thereby facilitating performing visual and/or X-ray transmission or reflection inspection and/or analysis at high magnification levels, effectively addresses the need for improved methodology for performing failure analysis leading to development of improved, low ohmic resistance, well-aligned, void-free, adherent ball contact/underlying via structures. Further, the means and methodology provided by the present invention enjoy diverse utility in the manufacture of numerous and various types of electrical and electronic devices and/or components utilizing ball contact/via combinations.

DISCLOSURE OF THE INVENTION

An advantage of the present invention is an improved method for simple, reliable, and rapid sample preparation of raised ball contact/underlying via combinations or structures of electrical or electronic devices or components, for performing visual and/or X-ray transmission or reflection-type radiographic inspection and/or analysis thereof at high magnification.

Another advantage of the present invention is an improved method for simple, reliable, and rapid sample preparation of BGA or flip-chip raised contact/underlying via structures of particular AOI's of semiconductor IC devices and/or package substrates therefor for performing high magnification, visual and/or X-ray inspection and/or analysis thereof.

Yet another advantage is an improved method for performing high magnification, visual and/or X-ray analysis of BGA or flip chip raised contact/underlying via structures of particular AOI's of semiconductor IC devices and/or package substrates therefor.

Additional advantages and other features of the present invention will be set forth in the description which follows and in part will become apparent to those having ordinary skill in the art upon examination of the following or may be learned from the practice of the present invention. The advantages of the present invention may be realized as particularly pointed out in the appended claims.

According to one aspect of the present invention, the foregoing and other advantages are obtained in part by a method for performing inspection and/or analysis of raised electrical contacts and associated underlying vias of an electrical or electronic device or component, which method comprises the sequential steps of:

(a) providing an electrical or electronic device or component having opposing first and second major surfaces, the first major surface including an array of closely spaced-apart raised electrical contacts with respective underlying vias;

(b) selecting an area-of-interest ("AOI") of said first major surface, the AOI including at least one of the raised electrical contacts with its respective underlying via;

(c) cutting through the electrical or electronic device or component from the first major surface to the second major surface thereof along two substantially parallel lines to separate therefrom an elongated strip including the AOI;

(d) mounting the elongated strip on a surface of a substrate; and (e) inspecting and/or analyzing the AOI including the at least one electrical contact with respective underlying via for presence of offset or misalignment, voids, and delaminations.

According to embodiments of the present invention, step (a) comprises providing a semiconductor integrated circuit ("IC") device package or a package substrate having a two-dimensional, row-and-column, grid-shaped array of raised, ball grid array ("BGA") or flip-chip contacts on the first major surface thereof, wherein adjacent rows and columns of the two-dimensional, grid-shaped arrays of raised contacts are spaced apart from about 200 to about 600 $\mu$m and the elongated strip formed in step (c) has a narrow width of from about 5 to about 15 mils.

According to particular embodiments of the present invention, adjacent rows and columns of the two-dimensional, grid-shaped arrays are spaced apart about 400 $\mu$m and the elongated strip formed in step (c) has a narrow width of about 10 mils.

According to embodiments of the present invention, step (b) comprises selecting at least one row or column of contacts of the two-dimensional, grid-shaped array of contacts as the AOI; and step (c) comprises cutting along two substantially parallel lines extending along the spaces between the selected at least one row or column of contacts and the adjacent rows or columns of contacts on both sides of the selected row or column, wherein step (c) comprises cutting utilizing a wire saw and further comprises trimming at least one end of the elongated strip to remove at least one unwanted area outside of the AOI.

According to embodiments of the present invention, step (d) comprises mounting the elongated strip including the AOI on an X-ray transparent substrate; and step (e) comprises inspecting and/or analyzing the AOI utilizing X-rays.

According to particular embodiments of the present invention, step (e) comprises performing an X-ray transmission or reflection-type radiographic inspection and/or analysis of the AOI, including, for example, positioning an X-ray source and an X-ray detector facing opposite surfaces of the elongated strip; step (d) comprises mounting the elongated strip on the substrate surface such that a first one of two opposing edge surfaces of the elongated strip which are formed as a result of performing cutting step (c) is adjacent the substrate surface and the second one of the two opposing edge surfaces of the strip formed as a result of performing cutting step (c) faces away from the substrate surface; and step (e) comprises, for example, positioning the X-ray source adjacent to and facing the second edge surface of the strip and positioning the X-ray detector beneath the substrate, facing the first edge surface of the strip.

According to other embodiments of the present invention, step (d) further includes installing the X-ray transparent substrate with the elongated strip mounted thereon in a rotatable/tiltable chuck or mount, the elongated strip being mounted on a glass or polymer-based substrate; and the mounting is accomplished by means of a transparent adhesive or double-sided transparent adhesive tape.

According to another aspect of the present invention, a method for performing inspection and/or analysis of raised electrical contacts and respective underlying vias of electrical devices and/or components comprises the sequential steps of:

(a) providing an electrical or electronic device or component having opposing first and second major surfaces, the first major surface including an array of closely spaced-apart raised electrical contacts with respective underlying vias, wherein the electrical device or component is a semiconductor integrated circuit ("IC") device package or package substrate having a two-dimensional, row-and-column, grid-shaped array of raised, ball-grid array ("BGA") or flip-chip contacts on the first major surface thereof;

(b) selecting an area-of-interest ("AOI") of the first major surface, the AOI comprising at least a portion of at least one of the rows and columns forming the grid-shaped array of contacts;

(c) cutting through the IC device package or circuit board from the first major surface to the second major surface thereof along two substantially parallel lines extending along the spaces between the portion of the selected at least one row or column of contacts and the adjacent rows or columns of contacts on both sides of the selected at least one row or column, to thereby separate therefrom an elongated strip including the AOI;

(d) trimming at least one end of the elongated strip to remove at least one unwanted area outside of the AOI;

(e) mounting the elongated strip including the AOI on a surface of an X-ray transparent substrate; and (f) performing X-ray radiographic inspection and/or analysis of at least one raised contact with respective underlying via of the AOI for determining presence of any misalignment, voids, and delaminations.

According to embodiments of the invention, adjacent rows and columns of the two-dimensional, grid-shaped arrays of raised contacts are spaced apart from about 200 to about 600 μm and the elongated strip formed in step (c) has a narrow width of from about 5 to about 15 mils.

According to further embodiments of the present invention, step (f) comprises performing X-ray transmission or reflection-type radiographic inspection and/or analysis of the AOL, including, for example, positioning an X-ray source and an X-ray detector as to face opposite surfaces of the elongated strip; step (e) comprises mounting the elongated strip on the surface of the X-ray transparent substrate such that one of two opposing edge surfaces of the elongated strip formed as a result of performing step (c) is adjacent the substrate surface and the second one of the two opposing edge surfaces of the elongated strip formed as a result of performing step (c) faces away from the substrate surface; and step (f) comprises positioning the X-ray source adjacent to and facing the second edge surface of the elongated strip and positioning the X-ray detector beneath the substrate, facing the first edge of the elongated strip, wherein step (e) further includes installing the X-ray transparent substrate with the elongated strip mounted thereon in a rotatable/tiltable chuck or mount.

Additional advantages and aspects of the present invention will become apparent to those skilled in the art from the following detailed description, wherein embodiments of the present invention are shown and described, simply by way of illustration of the best mode contemplated for practicing the present invention. As will be described, the present invention is capable of other and different embodiments, and its several details are susceptible of modification in various obvious respects, all without departing from the spirit of the present invention. Accordingly, the drawings and description are to be regarded as illustrative in nature, and not limitative.

BRIEF DESCRIPTION OF THE DRAWING

The following detailed description of the embodiments of the present invention can best be understood when read in conjunction with the following drawing, in which the various features are not drawn to scale but rather are drawn as to best illustrate the pertinent features, and in which like reference numerals are employed throughout to designate similar features, wherein.

DESCRIPTION OF THE INVENTION

Figure 1A:
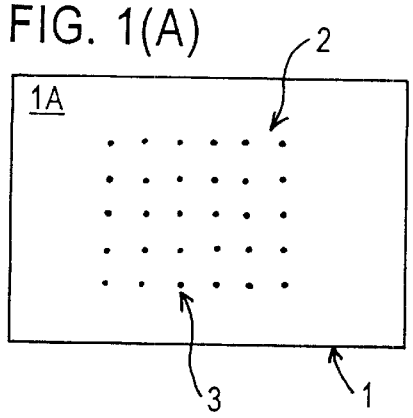
FIGS. 1(A)–1(F) schematically illustrate successive steps for performing the method according to the present invention.

The present invention is based upon the discovery that visual and/or X-ray transmission or reflection-type radiographic inspection and/or analysis of raised contact/underlying via structures and combinations, such as BGA and/or flip-chip contact arrays utilized in electrical and electronic devices and components, can be readily performed at high magnification, and without interference or clutter from extraneous structures, by selecting an area-of-interest (AOI) of the array of contacts, isolating the AOI, as by cutting, to form a narrow, elongated strip which is easily mounted on a substrate, e.g., a transparent substrate, thereby permitting close positioning of the radiation source to the AOI and affording very high magnification levels for examination of the internal structure of the raised contact/internal via combination. In addition, the small sample size, i.e., in the form of a narrow strip, facilitates mounting of the transparent substrate with the strip thereon in a rotatable/tiltable chuck of e.g., an X-ray radiographic analysis apparatus, thereby advantageously enabling variation of the viewing angle.

Referring now to FIG. 1, shown therein, in schematic form, are successive steps for performing the sample preparation and inspection/analysis method of the present invention. With particular reference to FIG. 1(A), in a first step according to the invention, there is provided a semiconductor integrated circuit (IC) device package or package substrate therefor (designated in each case by reference numeral 1), having a two-dimensional, row-and-column array 2 of raised, ball-grid array ("BGA") or flip-chip contacts 3 on a portion of a first major surface 1A thereof. At least some of the raised contacts 3 of array 2 overlie internal vias (not shown in the drawing) of the IC device package or circuit board 1 for electrical contact to a semiconductor IC chip or die therein or to underlying metallization level(s) of the circuit board. The raised solder balls or bumps of array 2 typically have diameters in the range of from about 100 to about 200 μm, and adjacent rows and columns of the two-dimensional array 2 are spaced apart from about 200 to about 600 μm, e.g., about 400 μm.

Figure 1B:
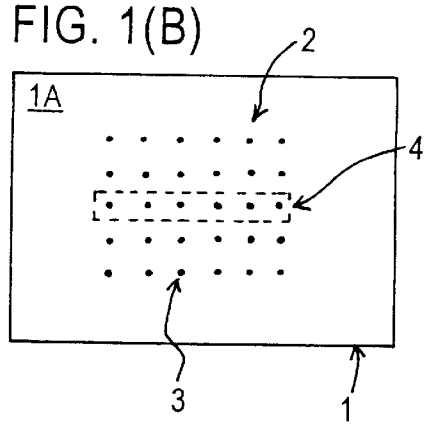

Referring now to FIG. 1(B), in the next step according to the inventive methodology, a particular area-of-interest ("AOI") 4 of array 2 is selected for inspection and/or analysis, based upon, for example, the nature of device failure or measurement of an electrical or other property indicating, e.g., poor ohmic contact in a particular area or raised contact/underlying via combination. AOI 4 may comprise at least a portion of one or more columns and/or rows of array 2 of raised contacts with respective underlying vias. By way of illustration, but not limitation, AOI 4 may comprise a single horizontally-oriented row of raised contacts/underlying via structures, as in the illustrated embodiment.

Figure 1C:
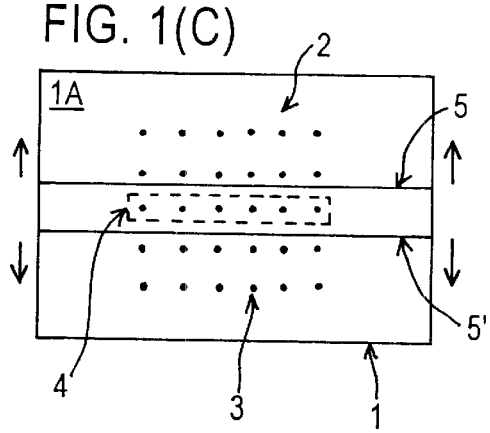
Figure 1D:
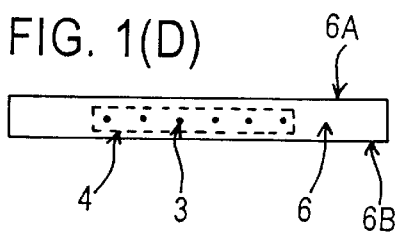

According to the next step of the invention, shown in FIG. 1(C), AOI 4 is separated from array 2 by cutting, as by use of a SiC or diamond-tipped wire saw or abrasive slurry, along parallel lines 5, 5' extending along the spaces between the selected row and the neighboring rows on both sides of the selected row, to form the narrow, elongated strip 6 shown in FIG. 1(D) and having opposed cut surfaces 6A, 6B. By way of example only, if adjacent rows of the array 2 are spaced apart by about 400 μm, cutting along lines 5, 5' with a conventional wire saw yields a narrow strip having a width between opposed cut surfaces 6A, 6B of from about 5 to about 15 mils, e.g., about 10 mils, depending upon the kerf loss.

Figure 1E:
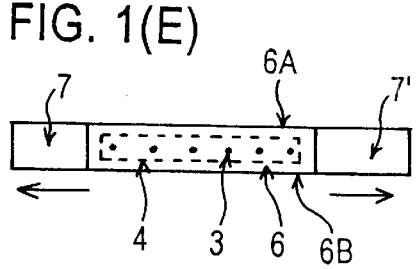

Adverting to FIG. 1(E), in an optional next step according to the invention, unwanted portions 7, 7' of strip 6 outside AOI 4 are trimmed from either or both ends thereof, by any convenient means, e.g., a wire saw.

Figure 1F:
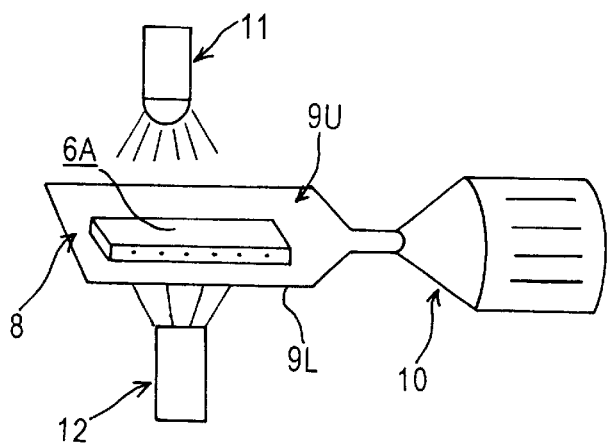

Referring now to FIG. 1(F), in an exemplary next step of the inventive methodology, the remaining portion of the elongated, narrow strip 6 including AOI 4 is mounted, via a transparent adhesive or double-sided transparent adhesive tape, to an elongated transparent substrate 8 having a flat planar mounting, or upper surface 9U, e.g., of glass or polymer-based material, one end of substrate 8 being secured for rotation and tilting about a longitudinally extending axis, e.g., by means of a rotatable/tiltable chuck 10 of an X-ray or visual measurement/analysis apparatus.

According to an embodiment of the present invention, elongated strip 6 is secured to upper surface 9U of substrate 8 via one of its opposing cut surfaces 6A or 6B and an X-ray or visual light source 11 is positioned above and closely adjacent the other, i.e., exposed, cut surface 6B or 6A, and an X-ray or other type radiation detector 12 is positioned beneath the lower surface 9L of substrate 8. Such arrangement facilitates obtaining, for example, high magnification, X-ray transmission images of the raised solder balls or bumps and their respective underlying internal vias, whereby the presence of any offsets or misalignments, voids, and layer separations (delaminations) is readily observable. The rotatable chuck 10 allows for performing X-ray transmission imaging at multiple viewing angles of the AOI 4 and the close positioning of the subject strip to the X-ray source 11 permits obtainment of well-defined images at high magnification, e.g., from about 500 to about 1,000 times magnification. Alternatively, X-ray reflection analysis may be performed utilizing an appropriately configured apparatus.

A number of advantages are thus provided by the inventive methodology, including, inter alia, simple, rapid, reliable, and sample preparation which effectively removes clutter, i.e., extraneous matter, from the subject field or area-of-interest (AOI). Moreover, the inventive sample preparation method involving formation of a narrow strip of material including the selected AOI, permits close positioning of an X-ray or other type radiation source to the subject, thereby facilitating obtainment of well-defined X-ray transmission or reflection or other type images at high magnification. In addition, the inventive methodology is conveniently performed without incurring significant additional expense. Finally, the present invention is not limited to use with semiconductor IC device packages and circuit boards therefor, but rather is applicable to performing rapid, reliable inspection and/or analysis of all manner of electrical devices and/or components having raised contact/underlying via or via-type structures.

In the previous description, numerous specific details have been set forth, such as specific materials, structures, processes, etc., in order to provide a better understanding of the present invention. However, the present invention can be practiced without resorting to the details specifically set forth. In other instances, well-known processing techniques and structures have not been described in detail in order not to unnecessarily obscure the present invention.

Only the preferred embodiments of the present invention and but a few examples of its versatility are shown and described in the present invention. It is to be understood that the present invention is capable of use in various other combinations and environments and is susceptible of changes and/or modifications within the scope of the inventive concept as expressed herein.

What is claimed is:

1. A method for performing inspection and/or analysis of raised electrical contacts and respective underlying vias of an electrical or electronic device or component, comprising the sequential steps of:

(a) providing an electrical or electronic device or component having opposing first and second major surfaces, said first major surface including an array of closely spaced-apart raised electrical contacts with respective underlying vias, wherein said electrical or electronic device or component is a semiconductor integrated circuit ("IC") device package or a package substrate having a two-dimensional, row-and-column, grid-shaped array of raised, ball-grid array ("BGA") or flip-chip contacts on said first major surface thereof and adjacent rows and columns of said two-dimensional, grid-shaped arrays of raised contacts are spaced apart from about 200 to about 600 $\mu$m;

(b) selecting an area-of-interest ("AOI") of said first major surface, said AOI including at least one said raised electrical contact with its respective underlying via;

(c) cutting through said electrical or electronic device or component from said first major surface to said second major surface along two substantially parallel lines to separate therefrom an elongated strip including said AOI, wherein said elongated strip has a narrow width of from about 5 to about 15 mils;

(d) mounting said elongated strip on a surface of a substrate; and (e) inspecting and/or analyzing said AOI including said at least one raised electrical contact with respective underlying via for presence of any misalignment, voids, and delaminations.

2. The method as in claim 1, wherein adjacent rows and columns of said two-dimensional, grid-shaped shaped array are spaced apart about 400 $\mu$m and said elongated strip formed in step (c) has a narrow width of about 10 mils.

3. The method as in claim 1, wherein:

step (b) comprises selecting at least one row or column of contacts of said two-dimensional, grid-shaped array as said AOI.

4. The method as in claim 3, wherein:

step (c) comprises cutting along two substantially parallel lines extending along the spaces between the selected at least one row or column of contacts and the adjacent rows or columns of contacts on both sides of the selected at least one row or column.

5. The method as in claim 4, wherein:

step (c) comprises cutting utilizing a wire saw.

6. The method as in claim 4, wherein:

step (c) further comprises trimming at least one end of said elongated strip to remove at least one unwanted area outside of said AOI.

7. The method as in claim 1, wherein:

step (d) comprises mounting said elongated strip including said AOI on an X-ray transparent substrate; and step (e) comprises performing inspection and analysis of said AOI utilizing X-rays.

8. The method as in claim 7, wherein:

step (e) comprises performing X-ray transmission inspection and/or analysis of said AOI, including positioning an X-ray source and an X-ray detector facing opposite surfaces of said elongated strip.

9. The method as in claim 8, wherein:

step (d) comprises mounting said elongated strip on said substrate surface such that a first one of two opposing edge surfaces of said elongated strip which are formed as a result of performing cutting step (c) is adjacent said substrate surface and the second one of the two opposing edge surfaces of said elongated strip formed as a result of performing cutting step (c) faces away from said substrate surface.

10. The method as in claim 9, wherein:

step (e) comprises positioning said X-ray source adjacent to and facing said second edge surface of said strip and positioning said X-ray detector beneath said substrate, facing said first edge surface of said strip.

11. The method as in claim 7, wherein:

step (d) further includes installing said X-ray transparent substrate with said elongated strip mounted thereon in a rotatable/tiltable chuck or mount.

12. The method as in claim 7, wherein:

step (d) comprises mounting said elongated strip on a glass- or polymer-based substrate.

13. The method as in claim 12, wherein:

step (d) comprises mounting said elongated strip on said substrate via a transparent adhesive or double-sided transparent adhesive tape.

14. A method for performing inspection and/or analysis of raised electrical contacts and respective underlying vias of electrical devices and/or components, comprising the sequential steps of:

(a) providing an electrical or electronic device or component having opposing first and second major surfaces, said first major surface including an array of closely spaced-apart raised electrical contacts with respective underlying vias, wherein said electrical device or component is a semiconductor integrated circuit ("IC") device package or a package substrate having a two-dimensional, row-and-column, grid-shaped array of raised, ball-grid array ("BGA") contacts or flip-chip contacts on said first major surface thereof;

(b) selecting an area-of-interest ("AOI") of said first major surface, said AOI comprising at least a portion of at least one of said rows and columns forming said grid-shaped array of contacts;

(c) cutting through said IC device package or circuit board from said first major surface to said second major surface thereof along two substantially parallel lines extending along the spaces between the selected row or column of contacts and the adjacent rows or columns of contacts on both sides of the selected at least one row or column, to thereby separate therefrom an elongated strip including said AOI;

(d) trimming at least one end of said elongated strip to remove at least one unwanted area outside of said AOI;

(e) mounting said elongated strip including said AOI on a surface of an X-ray transparent substrate; and (f) performing X-ray inspection and/or analysis of at least one raised contact with respective underlying via of said AOI for determining presence of any misalignment, voids, and delaminations.

15. The method as in claim 14, wherein adjacent rows and columns of said two-dimensional, grid-shaped arrays of raised contacts are spaced apart from about 200 to about 600 $\mu$m and said elongated strip formed in step (c) has a narrow width of from about 5 to about 15 mils.

16. The method as in claim 14, wherein:

step (f) comprises performing X-ray transmission inspection and/or analysis of said AOI including positioning an X-ray source and an X-ray detector facing opposite surfaces of said elongated strip.

17. The method as in claim 16, wherein:

step (e) comprises mounting said elongated strip on said surface of said X-ray transparent substrate such that one of two opposing edge surfaces of said elongated strip formed as a result of performing cutting step (c) is adjacent said substrate surface and the second one of the two opposing edge surfaces of said elongated strip formed as a result of performing cutting step (c) faces away from said substrate surface; and step (f) comprises positioning said X-ray source adjacent to and facing said second edge surface of said elongated strip and positioning said X-ray detector beneath said substrate, facing said first edge surface of said elongated strip.

18. The method as in claim 17, wherein:

step (e) further includes installing said X-ray transparent substrate with said elongated strip mounted thereon in a rotatable/tiltable chuck or mount.

* * * * *